United States Patent [19]

Damani et al.

[11] Patent Number: 4,514,385
[45] Date of Patent: Apr. 30, 1985

[54] ANTI-ACNE COMPOSITIONS

[75] Inventors: Nalinkant C. Damani; Haresh G. Bhagat; Ramon L. McElhaney, all of Fort Worth, Tex.

[73] Assignee: Alcon Laboratories, Inc., Fort Worth, Tex.

[21] Appl. No.: 308,385

[22] Filed: Oct. 5, 1981

[51] Int. Cl.$^3$ .................... A61K 31/78; A61K 31/605
[52] U.S. Cl. ..................................... 424/81; 514/164; 514/859
[58] Field of Search ......................................... 424/235

[56] References Cited

FOREIGN PATENT DOCUMENTS 2018589 10/1979 United Kingdom .

OTHER PUBLICATIONS

Caver, P. et al., Amer. Jour. Pharm., Apr. 1957.
Amino Acid Salts of Carbopol Resins TDS #53, The B. F. Goodrich Company.

Primary Examiner—Leonard Schenkman
Attorney, Agent, or Firm—Fitch, Even, Tabin & Flannery

[57] ABSTRACT

Anti-acne preparations include finely divided, dispersed particles of benzoyl peroxide and finely divided, dispersed particles of salicylic acid in an aqueous gel formed from carboxy vinyl polymer resins. The gels are prepared without loss of salicylic acid by fully hydrating the resin in an aqueous medium and allowing the resin to gel in the absence of an alkaline neutralizing agent.

6 Claims, No Drawings

ANTI-ACNE COMPOSITIONS

The present invention relates to therapeutic compositions for the treatment of acne and seborrhea.

BACKGROUND OF THE INVENTION

Acne and seborrhea are conditions of the human skin characterized by the excess flow of sebum (skin oil) from the sebaceous glands. The excess sebum may block or stagnate sebum flow through the hair follicle and thicken therein to form a solid plug known as a comedone. Formation of a comedone stimulates hyperkeratinization of the follicular opening, thus completely closing the duct. The usual result is a papule, a pustule, or a cyst, which becomes contaminated with bacteria such a P-acnes. The resulting infections characterize the disease state known as acne and, in lesser severity, seborrhea.

As described in U.S. Pat. No. 4,056,611, benzoyl peroxide is an antimicrobial agent effective against P-acnes. Salicylic acid is a known keratolytic agent which may be used to remove the horny outer layer of skin composed largely of a substance known as keratin. Salicylic acid also has comedolytic activity, i.e., the ability to dissolve and penetrate comedones, as well as some antimicrobial activity. It is reported in UK patent application GB No. 2018569A that benzoyl peroxide and salicylic acid, when used together at certain specified levels, exhibit a therapeutic effect greater than either agent alone in treating acne.

In solution, benzoyl peroxide and salicylic acid are incompatible with each other because benzoyl peroxide oxidizes salicylic acid, thereby reducing the amounts of both substances. Furthermore, while both benzoyl peroxide and salicylic acid are acceptably non-irritating to the skin, the oxidation products of salicylic acid are unacceptably irritating to the skin. It is desirable to have stable compositions for use as ointments or in toiletries as soaps, detergent bars, skin cleansers, shampoos etc. which contain both benzoyl peroxide and salicylic acid for use against acne.

Although salicylic acid and benzoyl peroxide might be incorporated in two preparations for sequential application, it is difficult to gain consumer acceptance for commercially distributed formulae other than single compositions. The compatibility problems of salicylic acid and benzoyl peroxide may be overcome by incorporating both substances in a composition as dispersed, finely divided particles. Such dispersions are possible in aqueous systems as both benzoyl peroxide and salicylic acid are generally insoluble in water. The above-mentioned UK Application teaches the dispersion of benzoyl peroxide and salicylic acid in aqueous compositions including gelling agents, such as methyl cellulose and thickening agents, such as Veegum K.

Attempts were also described in the above-mentioned UK Application to prepare compositions of benzoyl peroxide and salicylic acid in Carbopol 941. However, these attempts were less than successful, as it was not possible to prepare a uniform stable composition. Carboxy vinyl polymers such as those sold under the registered trademarks Carbopol 941, 940, and 934 of B. F. Goodrich Chemical Co. are recognized as particularly desirable pharmaceutical support vehicles. Carboxy vinyl polymers are generally unaffected by temperature variation within the temperature ranges in which pharmaceutical compositions are stored. They are not subject to hydrolysis or oxidation. Importantly, carboxy vinyl polymers are neither attacked by nor support bacteria or mold growth; however, they do not prevent growth and thus may be used in conjunction with an anti-bacterial and/or anti-fungal agent.

Carboxy vinyl polymers do not cause irritation to skin and produce only minimal irritation and no damage to ocular tissue. Although acne preparations are not intended for internal use, the fact that carboxy vinyl polymers have negligable toxicity (some, e.g., Carbopol 934, have been tested and approved for internal use) assures that inadvertent ingestion will not be harmful. Carboxy vinyl gels, when applied to the skin, rub in well and do not feel greasy or sticky. The gels also provide for ready absorption of the medicament and easy removal by soap and water.

Mucilages or gels of carboxy vinyl polymers are generally formed by dispersing particles of acidic carboxy vinyl polymer with an appropriate base, resulting in the immediate formation of a gel. In the above-mentioned UK Application, the base mentioned for use with Carbopol was diisopropanolamine. The less-than-successful results reported may be attributed to the chemical interaction between the salicylic acid and the basic amine. Stronger bases, e.g., NaOH, if used to gel carboxy vinyl resins, would be expected to result in even more unsatisfactory results.

Because of the demonstrated combined effect of benzoyl peroxide and salicylic acid against acne and seborrhea and the known desirability of carboxy vinyl resins as pharmaceutical supports, it is desirable to have stable dispersions of benzoyl peroxide and salicylic acid in carboxy vinyl polymer gels.

SUMMARY OF THE INVENTION

Anti-acne preparations are prepared having finely divided particles of benzoyl peroxide and salicylic acid dispersed in an aqueous carboxy vinyl polymer (carboxypolymethylene) gel. The general insolubility of benzoyl peroxide and salicylic acid in water enables these substances to be dispersed in the aqueous gel without significant reaction. The carboxy vinyl polymer resins are gelled in the absence of an alkaline neutralizing agent which would tend to react with salicylic acid.

DETAILED DESCRIPTION OF THE PREFERRED EMBODIMENTS

Benzoyl peroxide and salicylic acid, in sufficient amounts to be therapeutically effective and in proportions in which salicylic acid potentiates the antimicrobial characteristics of benzoyl peroxide, are suspended in an aqueous carboxy vinyl polymer gel. In accordance with the present invention, stable aqueous carboxy vinyl polymer gels containing both dispersed benzoyl peroxide and dispersed salicylic acid are achieved by allowing the carboxy vinyl resins to gel in the absence of an alkaline neutralizing agent which would react with the salicylic acid. The compositions contain between about 0.5 and about 25 percent and preferably between about 1 and about 10 percent by weight benzoyl peroxide, between about 0.1 and about 25 percent by weight salicylic acid, preferably between about 2 and about 10 per cent by weight of salicylic acid, and between about 0.1 and about 4 percent by weight of the resin. As the compositions are intended for pharmaceutical application, the benzoyl peroxide and salicylic acid are of high purity, i.e., over 95 percent by weight pure, and effectively free of impurities which are toxic or irritating to the skin.

Contrary to the accepted practice of preparing carboxy vinyl polymer gels, the gels are prepared without neutralization of a resin dispersion. Instead, successful gelling is achieved by fully hydrating the carboxy vinyl polymer resin in an aqueous medium before dispersing the active ingredients and relying in hydrogen bonding between the water and the resin to form the gel. Elimination of the neutralization step elminates the undesirable reactions of the neutralizing base with slicylic acid.

Benzoyl peroxide is only slightly soluble in water, and salicylic acid is soluble in water to the extent of 1.8 gm/L at 20° C. Accordingly, particles of salicylic acid and benzoyl peroxide may be dispersed in aqueous solutions with the resulting dispersion being relatively stable as there is little dissolved benzoyl peroxide or salicylic acid available to react. It has been found that compositions useful for toiletries may contain particles of benzoyl peroxide and salicylic acid dispersed in an aqueous-based medium in which the solubility of either agent is less than about 5 gm/L at 20° C. After the composition is applied to the skin, the particles of salicylic acid and benzoyl peroxide are dissolved and carried by the oils and fatty acids on the surface of the skin. So that the particles may be fully dissolved by the fluids of the skin surface, the particles are finely divided, and it is preferred that the average particle size of the benzoyl peroxide be less than about 60 mesh and that the average particle size of the salicylic acid be less than about 60 mesh.

Carboxy vinyl polymers are highly effective thickening agents and will form dispersion-supporting gels in concentrations as low as 0.1 percent. The concentration of the resin used depends on the desired thickness of the gel. Because gelling without a base does not result in gels as thick as are prepared by neutralization, additional resin is used to form gels of viscosity corresponding to base-neutralized gels. For purposes of this invention, the concentration of carboxy vinyl polymer resin is between about 0.1 and about 4.0 percent by weight of the compositions.

The compositions may also include up to about 30 percent by weight of a surfactant which, when the composition is applied to the skin, helps remove sebum and other oily substances from the skin and hair follicles so that the benzoyl peroxide and salicylic acid may intimately contact the skin and acne sites. Additionally, the surfactant may serve as a carrier or vehicle for transport of the benzoyl peroxide and salicylic acid particles to the acne site. Surfactants which may be advantageously used in the practice of the invention include, but are not limited to, sodium octoxynol-3 sulfonate, lauryl dimethyl amine oxide, dioctyl sodium sulfosuccinate, sodium lauryl sulfate, sodium alpha olefin sulfonate.

Chelating agents, in amounts up to about 0.3 percent by weight of the composition, such as ethylene diamine tetraacetate and pharmaceutically acceptable salts thereof may be used to stabilize the compositions. In addition, a minute amount of essence or fragrance may be added to the compositions to impart a pleasant fragrance thereto.

The followng examples are representative of therapeutic compositions prepared in accordance with the invention.

EXAMPLE I 900 ml of purified water is heated to 80° C., and 28 g of sifted Carbopol 940 resin is added slowly with stirring to prevent lumping. A milky white suspension is formed, and stirring is continued until a clear dispersion is formed, indicating that the resin is fully hydrated. 0.8 g of tetrasodium ethylene diamine tetracetate (Na$_4$EDTA) and 19 g of sodium octoxynol-3 sulfonate are added and dissolved. 20 ml of acetone and 20 ml of propylene glycol are added to the solution.

The solution is cooled to below 20° C. and transferred to a homogenizer where 75.0 gm of salicylic acid, which has been sifted through a 60 mesh screen, and 35 g of benzoyl peroxide, which has been sifted through a 60 mesh screen, are added along with sufficient additional water to bring the volume up to 1 liter. After a homogeneous dispersion is formed, the dispersion is poured into a beaker and is left undisturbed as it gels. After about 30 min., a creamy gel is formed which may be used as a skin ointment. The resulting creamy gel has the following composition expressed as percent by weight.

| | |
|---|---|
| Salicylic acid | 7.5 |
| Benzoyl peroxide | 3.5 |
| Carbopol-940 | 2.8 |
| Sodium octoxynol-3 sulfonate | 1.9 |
| EDTA tetrasodium | 0.08 |
| Propylene glycol | 2.0 |
| Acetone | 2.0 |
| Water | to 100 |

EXAMPLE II

A foaming skin and scalp cleanser is prepared in a similar manner to the skin ointment of Example I. The cleanser has the following composition expressed as percent by weight.

| | |
|---|---|
| Benzoyl Peroxide | 2.0 |
| Salicylic acid | 4.0 |
| Carbopol-940 | 2.0 |
| Sodium C14–C16 alpha olefin sulfonate | 30.0 |
| Dioctyl sodium sulfosuccinate | 3.0 |
| EDTA disodium | 0.2 |
| Water | to 100 |

Gels prepared according to the present invention are applied topically to the skin of the patient by rubbing onto the area being treated one or more times daily. The gels may also be incorporated into toiletries, such as shampoos, soap bars and detergent bars, whereby the medicaments are applied as the patient washes himself. Both salicylic acid and benzoyl peroxide particles are sufficiently soluble in the oily fluids on the skin that washing with such a toiletry will apply effective dosages to the skin.

Upon the first application of the composition to the skin, the salicylic acid begins to remove the horny outer layer of the skin and begins to disrupt the fatty, infected impactions of the acne comedones. The benzoyl peroxide acts against the bacteria at the surface and in those areas made accessible by the keratolytic and comedolytic activity of the salicylic acid.

While the benzoyl peroxide dissolved on the skin acts relatively quickly as an oxidant, the salicylic acid becomes firmly bound to the skin and continues its keratolytic and comedolytic activity between applications of the composition. The prolonged retention of salicylic acid on the skin is demonstrated by the fluorescence, under Wood's light, of skin to which such a composition has been applied and thereafter washed. Within about four hours after application of the composition, desquamation of the skin becomes observable and after about two to three days of treatment, generalized peeling occurs in the treated areas. Upon the second and subsequent applications of the composition, the benzoyl peroxide penetrates deeper into the acne comedones which have been penetrated by the salicylic acid to exert its antimicrobial activity against the bacteria deep within the comedones.

Although the salicylic acid and benzoyl peroxide are incompatible in solutions due to oxidation of the salicylic acid by the benzoyl peroxide, oxidation is not a problem when the two compounds are simultaneously applied to the skin from compositions that has the active compounds in suspensions. Because the oxidation of the salicylic acid is slow, the benzoyl peroxide is exhausted when the composition is applied to the skin before it significantly oxidizes the salicylic acid. While both benzoyl peroxide and salicylic acid are somewhat irritating to the skin, their combined use does not increase skin irritation beyond the predicted additive effects of the two compounds, and, as the salicylic acid potentiates the effectiveness of the benzoyl peroxide, lower dosages of each are required to be medically effective.

Compositions formulated according to this invention are stable at room temperature for over twelve months without significant oxidation of the salicylic acid by the benzoyl peroxide. Refrigerated below 4° C., such compositions are stable for over two years.

While the invention has been described in terms of certain preferred embodiments, modifications obvious to one skilled in the art may be made without departing from the scope of the present invention.

Various features of the invention are described in the following claims.

What is claimed is:

1. A stable single phase composition for the treatment of acne and seborrhea comprising:
   an aqueous gel of between about 0.1 and about 4.0 percent by weight of a fully hydrated carboxy vinyl polymer resin in the absence of an agent that gels said resin through neutralization, between about 0.1 and about 25 percent by weight finely divided particles of salicylic acid dispersed in said gel, and between 0.5 and about 25 percent by weight finely divided particles of benzoyl peroxide dispersed in said gel.

2. A composition in accordance with claim 1 wherein the average particle size of said benzoyl peroxide is less than about 60 mesh and wherein the average particle size of said salicylic acid is less than about 60 mesh.

3. A composition in accordance with claim 1 also including a chelating agent in amounts of up to about 0.3 percent by weight of said composition.

4. A composition in accordance with claim 3 wherein said chelating agent is EDTA or a pharmaceutically acceptable salt thereof.

5. A composition in accordance with claim 1 including up to about 30 percent by weight of a surfactant.

6. A method of suspending salicylic acid and benzoyl peroxide in carboxy vinyl polymer gels comprising dispersing a carboxy vinyl polymer resin in an aqueous medium and fully hydrating said resin, dispersing finely divided salicylic acid and finely divided benzoyl peroxide in said fully hydrated resin and allowing said resin to gel in the absence of an agent that gels said resin through neutralization.

* * * * *